(12) United States Patent
Beck

(10) Patent No.: US 6,319,240 B1
(45) Date of Patent: Nov. 20, 2001

(54) METHODS AND APPARATUS FOR OCULAR IONTOPHORESIS

(75) Inventor: Jon E. Beck, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/318,181

(22) Filed: May 25, 1999

(51) Int. Cl.[7] ................................................ A61N 1/30
(52) U.S. Cl. ........................ 604/501; 604/521; 604/20; 604/294
(58) Field of Search ............................ 604/20, 294, 521, 604/500, 501; 607/141; 128/383; 424/427–429

(56) References Cited

U.S. PATENT DOCUMENTS

| | | | |
|---|---|---|---|
| 542,508 | * | 7/1895 | Van Tuyl, Jr. . |
| 2,525,381 | * | 10/1950 | Tower . |
| 3,122,137 | * | 2/1964 | Erlanger . |
| 4,416,274 | | 11/1983 | Jacobsen et al. . |
| 4,564,016 | * | 1/1986 | Maurice et al. . |
| 4,708,716 | * | 11/1987 | Sibalis . |
| 4,955,378 | * | 9/1990 | Grasso . |
| 5,053,000 | * | 10/1991 | Booth et al. . |
| 5,160,316 | | 11/1992 | Henley . |
| 5,169,384 | * | 12/1992 | Bosniak et al. . |
| 5,174,304 | * | 12/1992 | Latina et al. . |
| 6,101,411 | * | 8/2000 | Newsome . |

FOREIGN PATENT DOCUMENTS

| | | |
|---|---|---|
| 9 390 19 | * 6/1982 | (SU) . |
| WO 99 40967 | 8/1999 | (WO) . |

OTHER PUBLICATIONS

Application for a Patent in France, No. 98–00009, Filed Jan. 5, 1998, in the name of OPTISINVEST, title: Device for Intraocular Transfer of Active Products by Iontophoresis, 14 pages, 5 pages of drawings.

Article on Regional Ocular Gentamicin Levels After Transcorneal and Transscleral Iontophoresis, Robyn E. Grossman, Douglas F. Chu, and David A Lee, Investigative Ophthalmology & Visual Science, vol. 31, No. 5, May 1990, pp. 909–916.

Report on Transscleral Iontophoresis of Gentamicin in Monkeys, Michael Barza, Cornelia Peckman, and Jules Braum, No. 6, pp. 1033–1036.

Article on The Role of Iontophoresis in Ocular Drug Delivery, Journal of Ocular Pharmacology, vol. 10, No. 1, 1994, David Sarraf and David A Lee, pp. 69–81.

Abstract of presentation entitled "Ocular Coulomb Controlled Iontophoresis," I. Nose, J–M. Parel, W. Lee, F. Cohen, Y. DeKosac, C. Rowaan, A. Paldano, V. Jallet, P. Söderberg, and J. Davis, referenced in Investigative Ophthamlmology & Visual Science, Feb. 15, 1996, vol. 37, No. 3., p. S41.

Article on "Iontophoresis of Dexamethasone in the Treatment of Endotoxin–Induced–Uveitis in Rats," Francine F. Berhar–Cohen, Jean–Marie Parel, Yves Pouliquen, Beatrice Thillaye–Goldenberg, Olivier Goureau, Silke Heydolph, Yves Courtois and Yvonne De Kozak, 1997, pp. 533–545.

\* cited by examiner

Primary Examiner—Mark Bockelman
(74) Attorney, Agent, or Firm—Factor & Partners

(57) ABSTRACT

An iontophoretic apparatus for ocular iontophoresis comprising a housing element formed to cooperate with the eye. In cooperation with the housing element is a flexible current distribution element that is capable of transmitting electrical current. Coupled to the current distribution element is a conformable medicament containment element that is filled with a medicament which is released under the influence of an electrical current, while a barrier element is provided that is configured to reduce current flow outside of the barrier and aid in the preferential delivery of medicament.

19 Claims, 10 Drawing Sheets

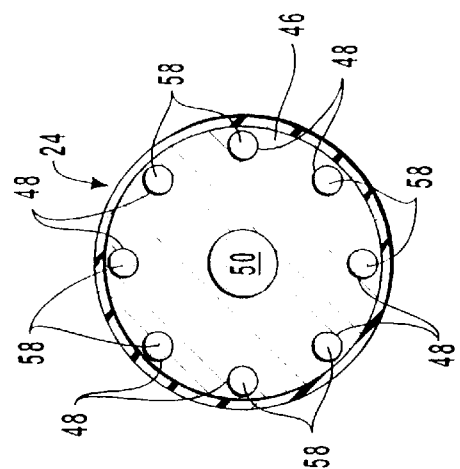
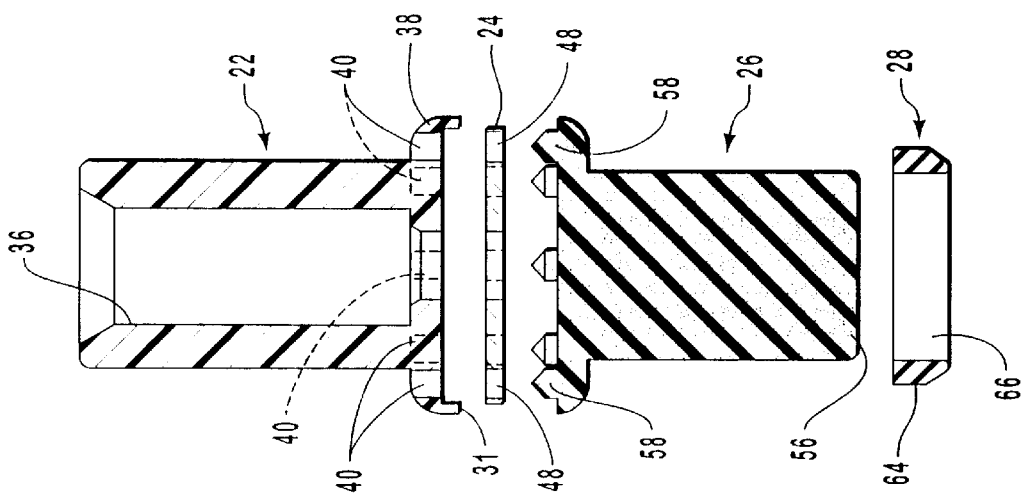
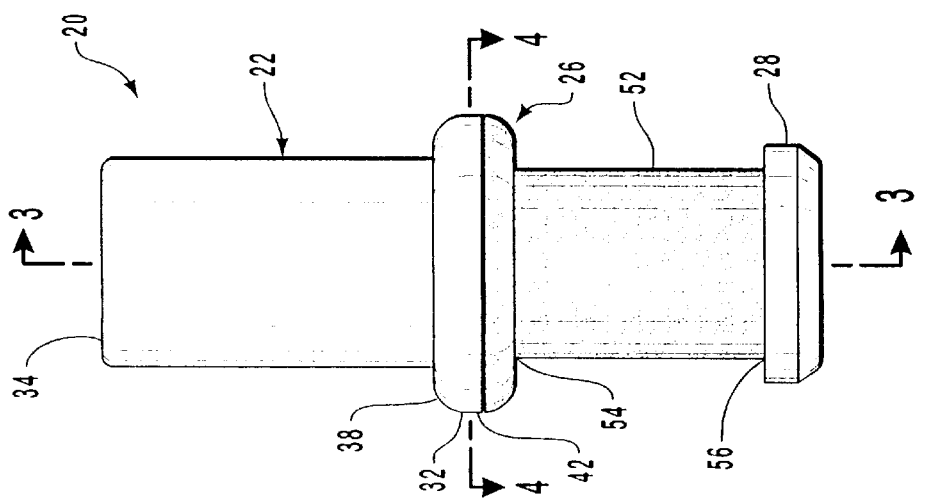

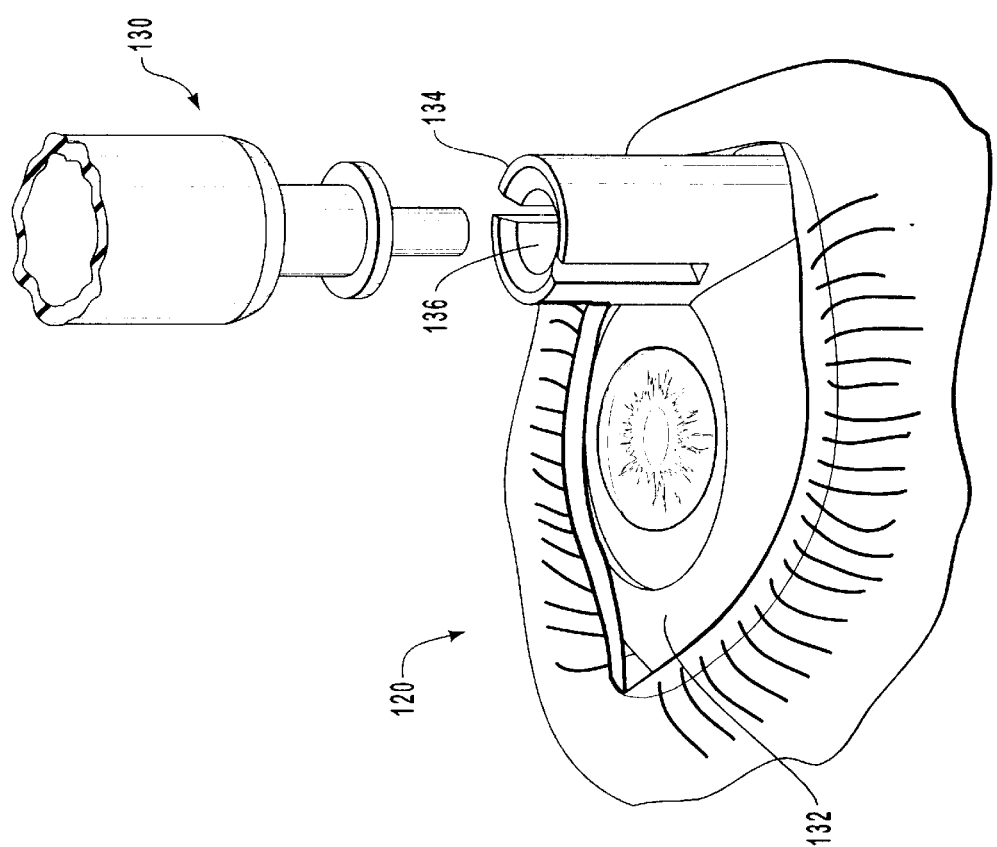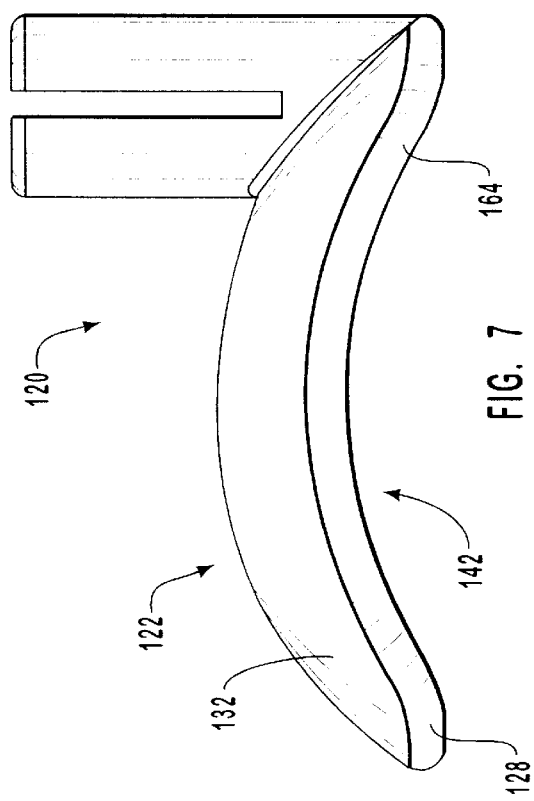

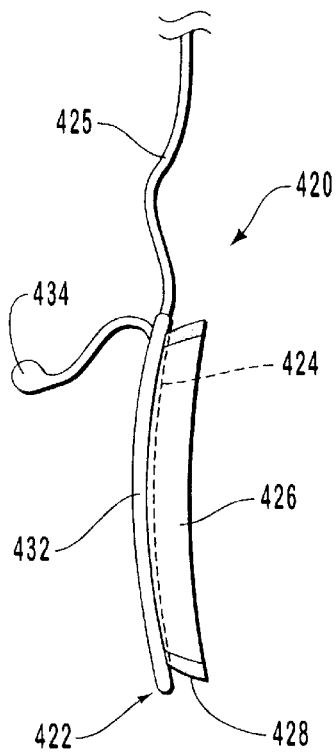
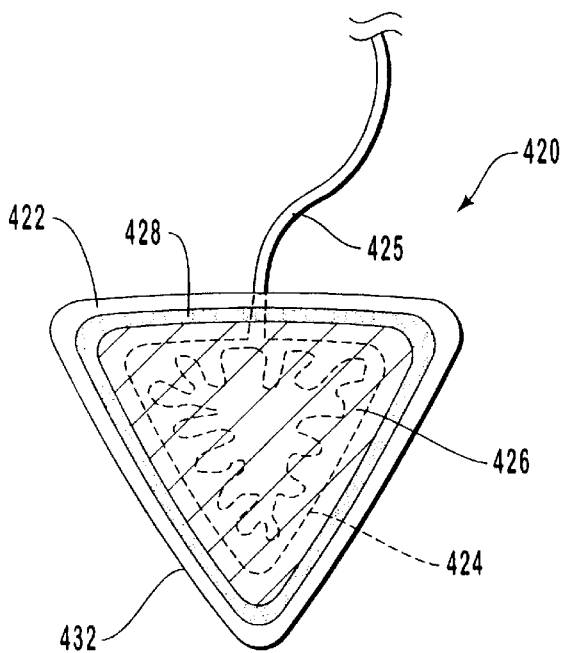
FIG. 14    FIG. 15
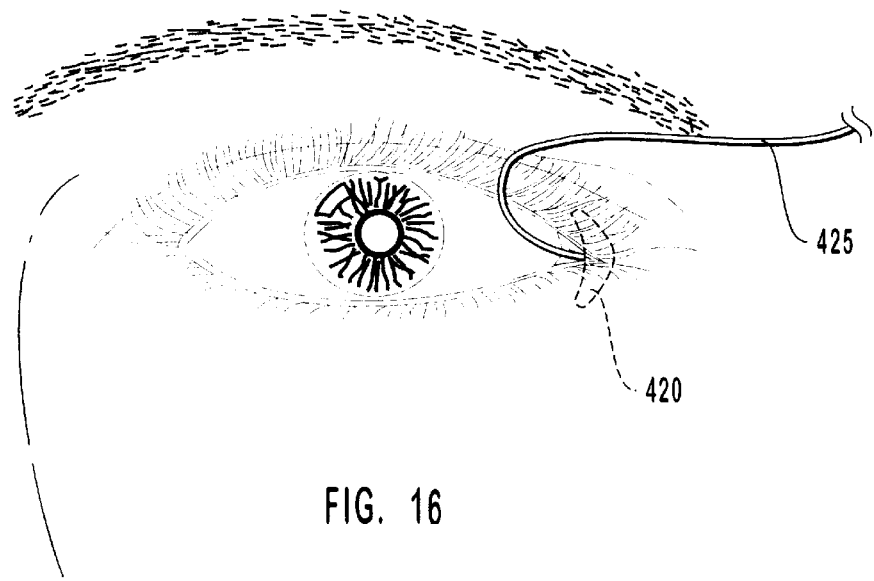
FIG. 16

METHODS AND APPARATUS FOR OCULAR IONTOPHORESIS

BACKGROUND OF THE INVENTION

1. The Field of the Invention

The present invention relates to methods and apparatus for administering substances to the eye. More particularly, the present invention discloses methods and apparatus for administering medicaments to the eye by iontophoresis.

2. The Relevant Technology

During ophthalmic medical procedures it is necessary to deliver a medicament to the eyeball, although the requirements for delivering medication to the eyeball vary depending on the particular medicinal purpose. For example, concentration levels of a medicament may be needed in the vitreous fluid of the interior of the eyeball to treat a particular affliction. However, for other pathological conditions, it may be efficacious to deliver and distribute medication over the entire surface of a sclera or to intra-sclera tissues. Yet another procedure may require an anesthetic compound to be carried or transmitted into the corneal tissue prior to a surgical procedure, such as keratotomy. Therefore, a given medical condition may require the delivery of a medicament over a widespread area, or conversely may need to be concentrated onto a smaller area.

One traditional method of delivering a medicament to the surface of the eye, either for treating a disorder or to aid in diagnosis, is through the use of eye drops. Generally, the lower eyelid is held away from the sclera and a drop of the medication is introduced into the gap formed between the eyelid and the sclera. During this procedure one must take care to avoid touching the eye with the dropper or one's fingers to reduce the risk of contamination. Through this procedure, numerous types of drug may be delivered to the eye, such as, antibiotics, corticosteroid, antihistamines. Additionally, eye drops may be used to administer drugs which control glaucoma and which either dilate or constrict the pupil. For example an ophthalmologist during an eye examination may drop tropicamide or phenylephrine onto the eye in order to dilate the pupil. By doing this the ophthalmologist will be able to fully view the crystalline lens and check for any defects. Furthermore, in cataract surgery, a physician may place a number of similar drops onto the surface of the eye in order to dilate the pupil so that most of the front surface of the lens is exposed. Additionally, a surgeon may use drops to introduce a local anesthetic instead of performing a local or general anesthetic with a needle.

Unfortunately, with the administration of medication through the use of an eyedropper there is the possibility of contamination, especially when multiple individuals use the same dropper. Furthermore, one may inadvertently contact the dropper with one's finger and thereby transmit any bacteria located on ones finger to the dropper. Additionally, medication may be required within the vitreous body of the eye, but the eyedropper only delivers medication to the surface of the eye and allows the medication to pass through the layers of the eye. The passage of medicament into the vitreous body may take a long period of time and hence reduce the effectiveness of eyedropper medicament delivery.

When a drug needs to be delivered below the surface of the eye, it is typical to utilize an injection. This is usually performed by inserting a needle into the tissue surrounding the eye or into the sclera of the eye. As a drug is injected into either region, it may be directed into the vitreous body or other surrounding tissue or other portions of the eye.

The use of a hypodermic needle, however, also has its disadvantages. Injection of a medicament is invasive, inconvenient and sometimes risky, due to the sharpness of the needle. As the physician inserts the needle into the surrounding tissues, a minor increase in the force applied may result in a perforated eyeball or a detached retina with the numerous associated problems. Additionally, many individuals are uneasy about the use of needles for any type of injection and more so when it involves inserting a needle close to or into the eye.

Another less common method used to administer a drug to an eye is known as iontophoresis. At the most basic level, iontophoresis involves the application of an electromotive force to drive ionic chemicals through a tissue so that they can be absorbed by adjacent tissues and blood vessels. In general terms, this is performed by placing a first bio-electrode containing an ionic medication solution in contact with a portion of the tissue which is to be phoresed. A second bio-electrode is placed on a part of the body near to the first bio-electrode, and a voltage is applied sufficient to cause current to pass through the tissue thereby completing the electrical circuit between the electrodes. As current flows, the ionized medication molecules migrate through the tissue under the influence of the second bio-electrode.

A similar approach is taken with respect to ocular iontophoresis, Traditionally ocular iontophoretic apparatus comes in one of two types, either an eyecup device or an applicator probe. The traditional eyecup device is formed from a half-spherical element. Normally the interior of the element is hollow and an electrode extends from the top of the half-spherical element. During iontophoresis, the eyecup is filled with a medicament solution and placed on the eye. As the voltage from a power source is applied, current passes from the electrode within the half-spherical element and flows into the surface of the eye. Simultaneously, the medicament ions are forced either from the cathodic bio-electrode within the half-spherical element towards the anodic bio-electrode, or vice versa, thereby forcing the medicament into the eye of the patient.

In an alternative ocular iontophoretic device, an applicator probe may be used. An applicator probe has an electrode which extends into a probe end that is filled with a medicament. The probe end is placed on the patient's afflicted area and medicament migrates from the probe end into the patient's tissue as current is applied.

Conventional ocular iontophoretic apparatus have a number of problems. For example, an applicator probe device requires one to precisely and continuously hold the probe against the patient's eyeball. Unfortunately, if the entire eyeball has to be phoresed this procedure can take a long period of time. Additionally, if one applies too great a force, too high a current, or maintains contact for too long a period of time, the patient's eyeball can be burned leaving lesions on the eye surface. Furthermore, with the eyecup-type apparatus, there is a possibility that one may scratch the eyeball of the patient if the probe is too long or if placement is not accurate. Also medication which is placed within the eyecup may escape from beneath the edges of the eyecup due to conformability limitations of the eyecup and variations in the size and curvature of the eyeball, Additionally, contaminants, such as tears, saline, or other impurities may infiltrate the medicament thereby reducing the potency or pharmacological effectiveness of the medicament. The eyecup may be forced against the surface of the eye to reduce the effects of leaking and containment infiltration, however, the required force may damage the eye.

Perhaps the most significant problem with prior ocular iontophoretic devices is the unintentional delivery of medicament to the surrounding soft tissues, including the eyelid, socket, etc, instead of to the eyeball or sclera. This inadvertent drug delivery to the surrounding tissues is due to the sclera and other eyeball tissues being wetted with conductive saline or tears. The saline or tears has considerably lower electrical resistance than alternative transscleral pathways, resulting in the electrical current preferentially following a pathway to the surrounding soft tissues.

It would be an advantage, therefore, to provide an apparatus which may be used to administer medicaments to any region of an eyeball, while preventing inaccurate distribution of medicament to surrounding tissues and damage to the eye.

SUMMARY AND OBJECTS OF THE INVENTION

It is, therefore, an object of the present invention to provide an apparatus for delivering a quantity of medicament to the eye.

It is another object of the present invention to prevent loss of medicament potency by more preferentially directing the delivery of a quantity of medicament to a specific region or regions requiring treatment.

It is yet another object of the present invention to provide an apparatus that reduces the effects of electrical shunting of the medicament over the surface of the eye and into the surrounding soft tissues.

Yet another object of the present invention is to provide an apparatus that prevents inflow of saline or tears into the medicament and drug matrix thereby preventing contamination of the medicament and drug matrix.

Still yet another object of the present invention is to provide an apparatus which prevents medicant delivery to tissues surrounding the eyeball.

It is another object of the present invention to provide an apparatus which may be hand-held by a user or fixably connected to a patient.

It is still yet another object of the present invention to provide an apparatus which prevents the possibility of damage to the eyeball during medicament delivery.

Yet another object of the present invention is to provide an apparatus which minimizes the time and discomfort necessary for iontophoresis by increasing the effectiveness of medicament delivery.

Yet another object of the present invention is to provide an apparatus which is flexible and capable of conforming to the surface upon which it is placed.

Yet another object of the present invention is to provide an apparatus which may be disposable or reusable.

To achieve the foregoing objects, and in accordance with the invention as embodied and broadly described herein, the present invention is an iontophoretic apparatus for ocular iontophoresis. The iontophoretic apparatus comprises a housing element formed to cooperate with the eye. Coupled to the housing element is a flexible current distribution element that is capable of transmitting an electrical current from a power source. In cooperation with the current distribution element is a conformable medicament containment element that is filled with a medicament. The medicament is released under the influence of an electrical current, while a barrier element is provided that is configured to reduce current flow outside of the barrier and hence prevent unwanted migration of the medicament.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 2 is a side view of one embodiment of an iontophoretic apparatus of the iontophoretic system.

FIG. 3 is an exploded cross-sectional view of the iontophoretic apparatus in FIG. 2 taken along the line 3—3.

FIG. 4 is a cross-sectional view of the iontophoretic apparatus in FIG. 3 taken along the line 4—4.

FIG. 7 is a side view of the embodiment of FIG. 6.

FIG. 8 is a perspective view of the embodiment of FIG. 6 shown in use.

FIG. 14 is a side view of yet another embodiment of the iontophoretic apparatus of the present invention.

FIG. 15 is a plan view of the embodiment of FIG. 14.

FIG. 16 is a plan view of the embodiment of FIG. 14 in use.

DETAILED DESCRIPTION OF THE PREFERRED EMBODIMENTS

The present invention relates to an iontophoretic system which is used to administer medicament to an eye. The iontophoretic system includes an iontophoretic apparatus which may be used to administer a medicament to an eye. The iontophoretic apparatus is configured such that medicaments arc preferentially delivered only to those areas which require the medicament. The iontophoretic apparatus allows a bio-electrode with a larger diameter than previously capable of being used in the delivery of a medicament. The increased diameter bio-electrode may be used without a loss in the penetration of a medicament into the eyeball.

Furthermore, the iontophoretic apparatus is configured to be easily used by an operator and/or fixably positioned in communication with the eye.

Figure 1:
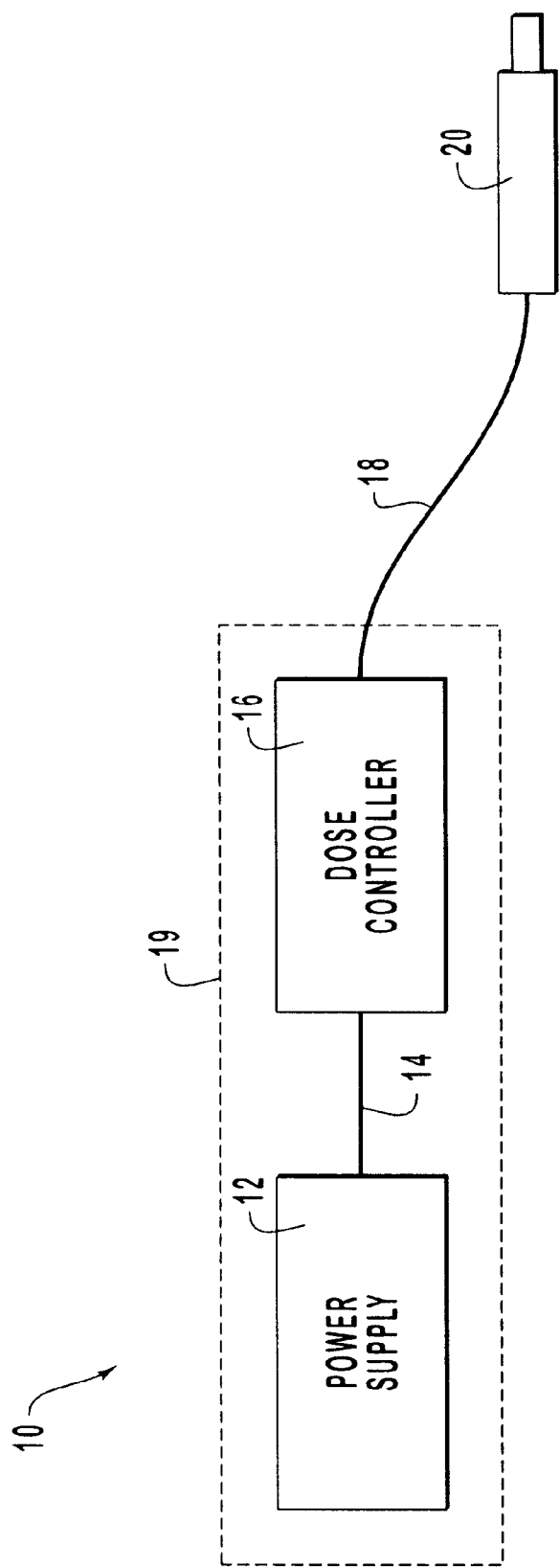
FIG. 1 is a schematic depiction of an iontophoretic system.

In general terms, as shown in FIG. 1, an iontophoretic systems 10 includes an electrical current source or a power supply 12 that is electrically connected to a dose controller 14 by way of a cable 16. Dose controller 14 is in turn electrically connected to an iontophoretic apparatus 20 by way of cable 18. The power supply 12 and dose controller 14 are well known in the art and perform the functions of providing and controlling various iontophoretic system properties such as, by way of example and not limitation, flow of electrical current, time of treatment, power cycling of treatment, strength of treatment, starting and/or pausing of treatment, and ramping of treatment current from an initial current to a steady state medicament delivery current. Power supply 12 and dose controller 16 may be formed from separate units which are coupled together by various electrical techniques, such as cable 16, or may be integrally formed in a single unit as represented by dotted line 19. As such, one skilled in the art can, in view of the teaching contained herein, identify various other embodiments and configurations of power supply 12, dose controller 16 and methods of coupling thereof, such that they may cooperate with iontophoretic apparatus 20. The subsequent discussion contained herein will be directed to the various configurations and embodiments of iontophoretic apparatus 20 which may be used in cooperation with various power supplies and/or dose controllers.

FIGS. 2–5 depict an iontophoretic apparatus 20 that may be used to perform localized iontophoresis to particular areas of the body and cooperate with the iontophoretic system. As shown generally in FIG. 5. iontophoretic apparatus 20, such as an application probe, is used to perform iontophoresis of the eye. It can be appreciated that iontophoretic apparatus 20 cooperates with the known elements of an iontophoretic system, such as a power supply and a dose controller (not shown) Generally speaking, iontophoretic apparatus 20 includes a housing element 22, a current distribution clement 24. a medicament containment element 26, and a barrier element 28. It can be appreciated that many other variations of iontophoretic apparatus 20 may also effectively carry out the intended function thereof.

According to one aspect of the present invention, housing element 22 comprises a first end 32, a second end 34, and a connector recess 36. Preferably, housing element 22 has a generally tubular form, where first end 32 has a greater cross-section than second end 34. First end 32 has a flange 38 located around the peripheral edge of first end 32. Flange 38 has a plurality of apertures 40 therethrough which allow current distribution clement 24 and medicament containment element 26 to be coupled thereto. Connector recess 36 is formed substantially through the center of housing element 22 from first end 32 to second end 34. Additionally, connector recess 36 extends outwardly from the center of housing element 22 thereby bisecting second end 34 of housing element 22 into two portion. It will be appreciated, in view teachings contained herein, that one skilled in the art can identify various other configurations of housing element 22 and its associated features.

For example, first end 32 may have the same cross-section as second end 34, or first end 32 may have a smaller cross-section than second end 34. Connector recess 36 may have different configurations dependent on the type of connection required between housing element 22 and a user handling device 30. For example, connector recess 36 may have an internal thread which interconnects with an associated thread on user handling device 30. In another alternative configuration, connector recess 36 may be tapered such that it may slip-fit with an associated tapered user handling device 30. Also, connector recess 36 may divide second end 34 into numerous sections dependent on the connector used to attach housing element 22 to user handling device 30. Various other means of connecting housing element 22 to the user handling device 30 are known to one skilled in the art. Additionally, in view of the teaching contained herein, one skilled in the art can identify numerous alternative configurations of housing element 22 which will perform the intended function thereof.

In general, housing element 22 is configured to securely hold current distribution element 24, medicament containment element 26, and barrier element 28 if needed, while being able to connect with user handling device 30. Housing element 22 is further configured to withstand forces applied by the user during iontophoresis.

Housing element 22 is preferably composed of materials which will be easily manufactured while giving sufficient strength, rigidity, and connecting possibilities for housing element 22. The types of material may range from plastics, metals, composites, Teflon, nylon, polyester, polyethylene, and polycarbonates and the like. It is preferred that housing element 22 be substantially composed of a polycarbonate plastic.

Coupled to housing element 22 is current distribution element 24. In one preferred embodiment, current distribution element 24 has a generally circular portion 46, have a disk shape similar to that of a washer. A plurality of holes 48 are located near the peripheral edge thereof, to allow current distribution element 24 to be coupled to first end 32 of housing element 22. Additionally, a center orifice 50 passes through the center of circular portion 46. It can be appreciated, in view of the information contained herein, that one skilled in the art can identify various other configurations of current distribution element 24.

For example, current distribution element 24 may have various shapes, such as, oval, rectangular, octagonal, trapezoidal or the like. Current distribution element 24 may be interconnected with housing element 22 while being fixably attached to user handling device 30. In such a case, current distribution 24 may be a protruding wire that extends from proximal end 31 of user handling device 30 and is configured to couple with medicament containment element 26. Current distribution element 24 is further formed to allow the external power source to electrically connect with the current distribution element 24. As such, current distribution element 24 may have any form known by one skilled in the art which allows an electrical connection between housing element 22, power source and medicament containment element 26. Current distribution element 24 therefore, requires sufficient strength, rigidity, temperature resistance, and electrical conductivity properties to resist damage when current is applied thereto. Various other configurations of current distribution element 24 are also effective in carrying out the intended function thereof.

Current distribution element 24 is preferably composed of materials which will be flexible while still being able to conduct electrical current. These may comprise, for example, aluminum, copper, thin films of metallic substances, carbon conductive films, carbon conductive printable films, other printed films, or the like. It is preferred that current distribution element 24 be formed of a thin metallic film printed on a plastic sheet or polyester film. The thickness of the plastic sheets or films ranges from about 2 mils to about 5 mils. It is preferred that the thickness be from about 3 mils to about 4 mils. It is more preferred that the thickness be approximately 3 mils.

In addition to the dimensions of current distribution element 24 alternate embodiments may be disposable or reusable. Therefore, different chemical compounds or metallic alloys way be used to provide cost effective means of delivering electrical current. If pH control is desired, then either silver ("Ag") or silver chloride ("Ag/AgCl") compounds can be used. For a reusable device, a cathodic current distribution element 24 could be made of a sintered version of Ag/AgCl, for example, to provide adequate Cl for several treatment applications. An anodic current distribution element 24 could be made from solid Ag metals or sintered Ag particles or inks, etc. If Ag or Ag/AgCl is desired for single-use disposable iontophoretic apparatus, then small amounts of Ag or Ag/AgCl could be employed in the form of pleated or printed ink-type films or the like. In other configurations of the present invention carbon conductors may be used as either anodic or cathodic current distribution element 24.

Coupled to current distribution element 24 is medicant containment element 26. In the embodiment of FIGS. 2–5, medicament containment element 26 has a generally cylindrical portion 52 having a first containment end 54 and a second containment end 56. First containment end 54 is connected to both current distribution element 24 and housing element 22. First containment end 54 has the same cross-section as that of first end 32 of housing element 22. Additionally, first containment end 54 has a plurality of protruding portions 58 near the peripheral edge thereof, which extend from first containment end 54 parallel to the longitudinal axis of medicament containment element 26. The plurality of protruding portions 58 pass through the plurality of holes 48 and lock within a corresponding plurality of apertures 40. The plurality of protruding portions 58 are configured to more efficiently transfer electrical current from current distribution element 24 to medicament containment element 26. It will be appreciated that medicament containment element 26 may have various other configurations that are also effective in carrying out the intended function thereof.

In general, medicament containment element 26 is configured to hold a supply of medicament during the iontophoresis procedure. Furthermore, medicament containment element 26 provides for the transfer of electrical current from current distribution element 24 to the surface in which it is in contact. Medicament containment element 26 retains the requisite strength and rigidity to elastically deform during iontophoresis while being pliable to thereby not damage the eye during contact therewith.

Various other configurations of medicament containment element 26 can be identified by one skilled in the art in view of the teachings herein. For example, the cross-section of medicament containment element 26 may vary depending on the manner by which medicament containment element 26 is coupled to either both current distribution element 24 and housing element 22 or to each one individually. Medicament containment element 26 may have the same cross-sectional profile as that of housing element 22 or current distribution element 24. In another alternate configuration, medicament containment element 26 may be cone-shaped with a conic aperture partially through the center thereof. The conic's aperture is configured to cooperate with current distribution element 24 when it is fixably attached to user handling device 30 and has the form of a protruding wire that extends from proximal end 31 of user handling device 30. Medicament containment element 26 may also have any cross-section or dimensions necessary to perform a specific type of iontophoresis, such as, rounded, angled, pointed and the like. Furthermore. medicament containment element 26 may have a cross section of only a few millimeters or a few centimeters depending on the particular use. The dimensions may range from 1 mm to 20 mm. It is preferred that medicament containment element 26 be approximately between about 5 mm and 6 mm.

One example of material structure capable of performing the function of medicament containment element 26 is a gel sponge composite containment matrix as defined in U.S. Pat. No. 5,558,632 issued to Lloyd et al., which is incorporated herein by reference. Various other materials used to form medicament containment element 26 are also effective in carrying out the intended function thereof. For example, a variety of reusable or single use disposable porous wicking materials, hydrogels, or composite materials may be used.

For ocular iontophoresis, it is preferable that a cross-linked hydrogel be used since the cohesive nature of the cross-linked hydrogel prevents fibrous material, gels or residues being left on the eye after iontophoresis. The use of a cross-linked hydrogel also is beneficial during iontophoresis since no fibrous materials may abrade or irritate the eye. For alternative uses of iontophoresis apertures such as for treating skin or hair follicles, a gel which would wick and wet effectively would be preferable. Examples of such materials for alternative uses includes a hydrogel impregnated dry sponge matrix, and a multi-laminate cross-linked polyethylene oxide dried matrix.

Various types of medicament may also be used in medicament containment element 26 dependant on the type of medical procedure which is to be performed. For example, anesthetics such as lidocaine may be contained within medicament containment element 26 Another example is oligonucleutides, such as Vascular Endothelial Growth Factors or VEGF inhibitors. Other illustrative examples of drugs which may be used include antibiotics, corticosteroids, antihistamines, tropicamide, or phenylephrine. Various other medicaments may also be transmitted through the use of iontophoretic apparatus 20.

As shown in FIGS. 2–5, barrier element 28 is coupled to medicament containment element 26. Barrier element 28 has a toroidal form or doughnut shape having a barrier body 64 configured with a first recess 66 having an axis coinciding with the axis of barrier body 64, A portion of first recess 64 connects with medicament containment element 26, while another portion cooperates with a portion of the eyeball. Various other configurations of barrier element 28 are also effective in carrying out the intended function thereof.

In general, barrier element 28 is formed to connect with medicament containment element 26 and aid in the preferential delivery of medicament. It is a feature of the present invention to provide preferential delivery during ocular iontophoresis to avoid the problems of electrical pathway shunting described previously.

It is believed that electrical pathway shunting occurs when an electrical current is applied to the eyeball, resulting in the electrical current radiating in many directions at the same time. Under traditional electrical theory, current or flow of charge will follow the path of least resistance. With ocular iontophoresis, since the surface of the eyeball is continuously bathed in an electrically conductive ionic saline, tears and natural occurring saline will distribute the current throughout the surface of the eyeball and into surrounding tissues. This effect is believed to occur regardless of the exact location on the eyeball surface where the electrical current is introduced. Therefore, current may flow into the sclera, into the vitreous body of the eyeball, or even into the surrounding facial tissues, such as the inner eyelid and socket tissues. Recent studies support this proposition. In an attempt to deliver a drug compound via transscleral iontophoresis, substantially no levels of drug compound were detected in the vitreous of the eye, while considerable blood systemic levels of the compound were detected. This suggests that the drug compound and electrical driving current are being diverted or "shunted" from transscleral flow to travelling along the surface of the eyeball into nearby soft tissue. Barrier element 28 of the present invention is formed to aid in preventing medicament from following the electrical pathways on the surface of the eyeball thereby assisting with preferential distribution of the medicament for specific medical procedures.

Barrier element 28 may have various configurations dependent on the size and dimensions of medicament containment element 26, current distribution element 24, housing element 22 and the particular medical procedure involved. For example, iontophoretic apparatus 20 may not require barrier element 28 since a medical procedure may use electrical pathway shunting to aid in the distribution of medicament. Iontophoretic apparatus 20 may have more than one barrier element 28, thereby creating a sealed area between the first and second barrier elements which more effectively and preferentially delivers medicament. Barrier element 28 may have triangular-shape, circular, oval-shaped, or the like. It will be appreciated that various other configurations may be used and are known by one skilled in the art, in view of the teachings contained herein.

Barrier element 28 is preferably composed of materials which will provide sufficient resilience to flexing while being flexible to conform to the surface upon which it makes contact with to thereby form a fluid-tight seal. The types of material which may be used for barrier clement 28 include soft silicone gels or other types of silicon compounds which generally conform to the surface upon which they are placed. For example, Dow Q7-2218 two-part soft silicone gel, silicone and elastomer equivalents from Nusil, low durometer urethanes, and similar materials are useful in the construction of barrier element 28. It is preferred that barrier element 28 be composed of low-durometer silicone elastomeric gels.

In forming iontophoretic apparatus 20 it is necessary to connect the above described elements together. There are a variety of methods to accomplish the bonding or joining of the individual elements. For example, housing element 22 may be sonically bonded, glued, screwed or bolted to medicament containment element 26 and current distribution element 24. Barrier element 28 may be attached to medicament containment element 26 through the use of adhesives or the like. Various methods of bonding the elements of iontophoretic apparatus 20 together, in view of the teaching contained herein, can be identified by one skilled in the art. It is preferred that the elements be sonically bonded together.

Figure 5:
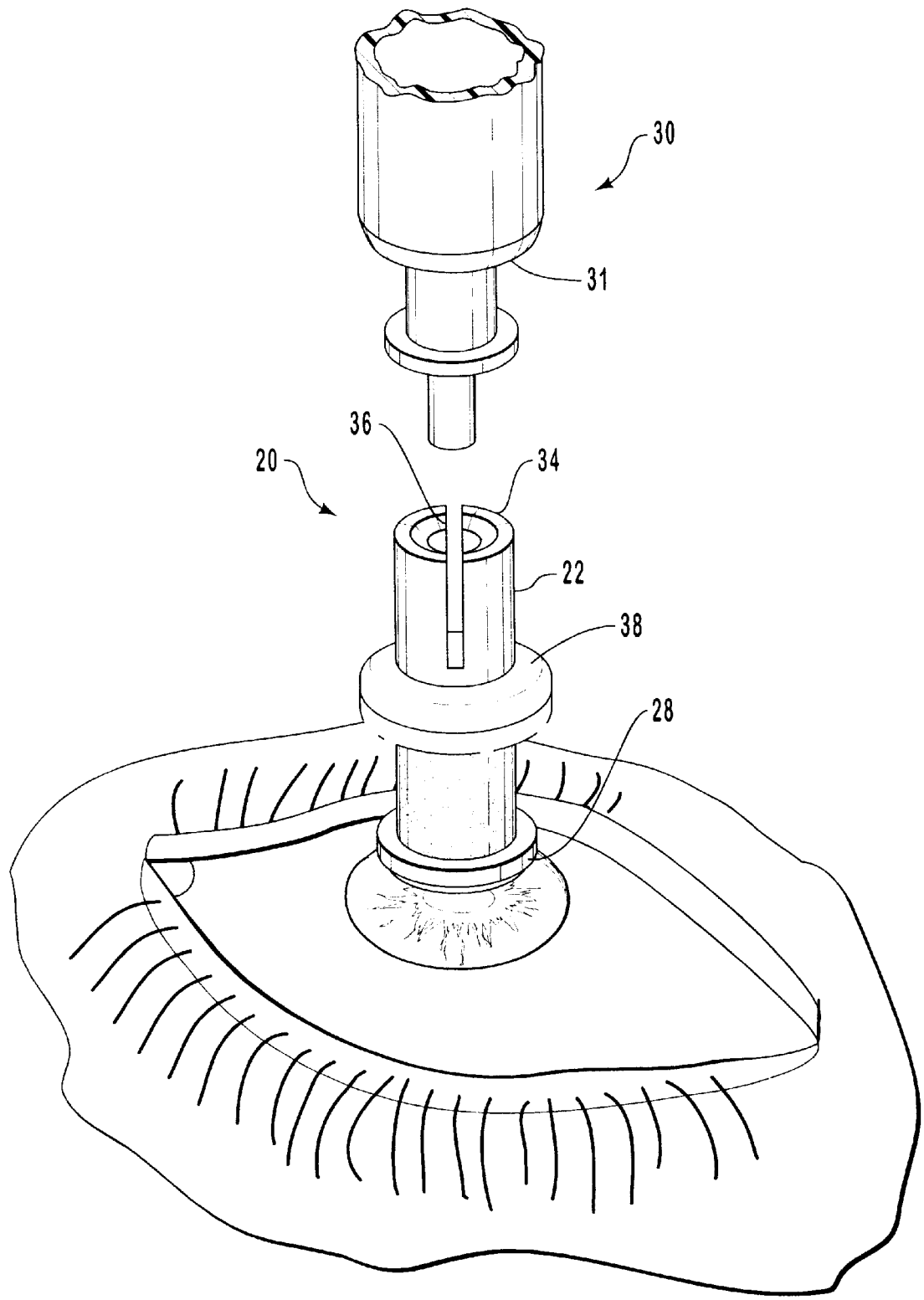
FIG. 5 is a perspective view of the iontophoretic apparatus in FIG. 2 in use.

Referring now to FIG. 5, iontophoretic apparatus 20 may be used to phorese the eyeball. In operation, an electrical current is applied through connector recess 36, to current distribution element 24. The current then travels through medicament containment element 26 into the eyeball. The current is drawn through the eyeball as it travels to a second bio-electrode which is located near the eye. Barrier element 28 comes into contact with the eyeball as iontophoretic apparatus 20 is placed against the eye. Barrier element 28 reduces the electrical current which passes along the surface of the sclera or conjunctiva and hence directs the delivery of medicament to the area within the confines of barrier element 28. As shown in FIG. 4 iontophoretic apparatus 20 may have a similar dimension to that of the visible iris, although various other dimensions and sizes are also effective in carrying out the intended function described herein.

Figure 6:
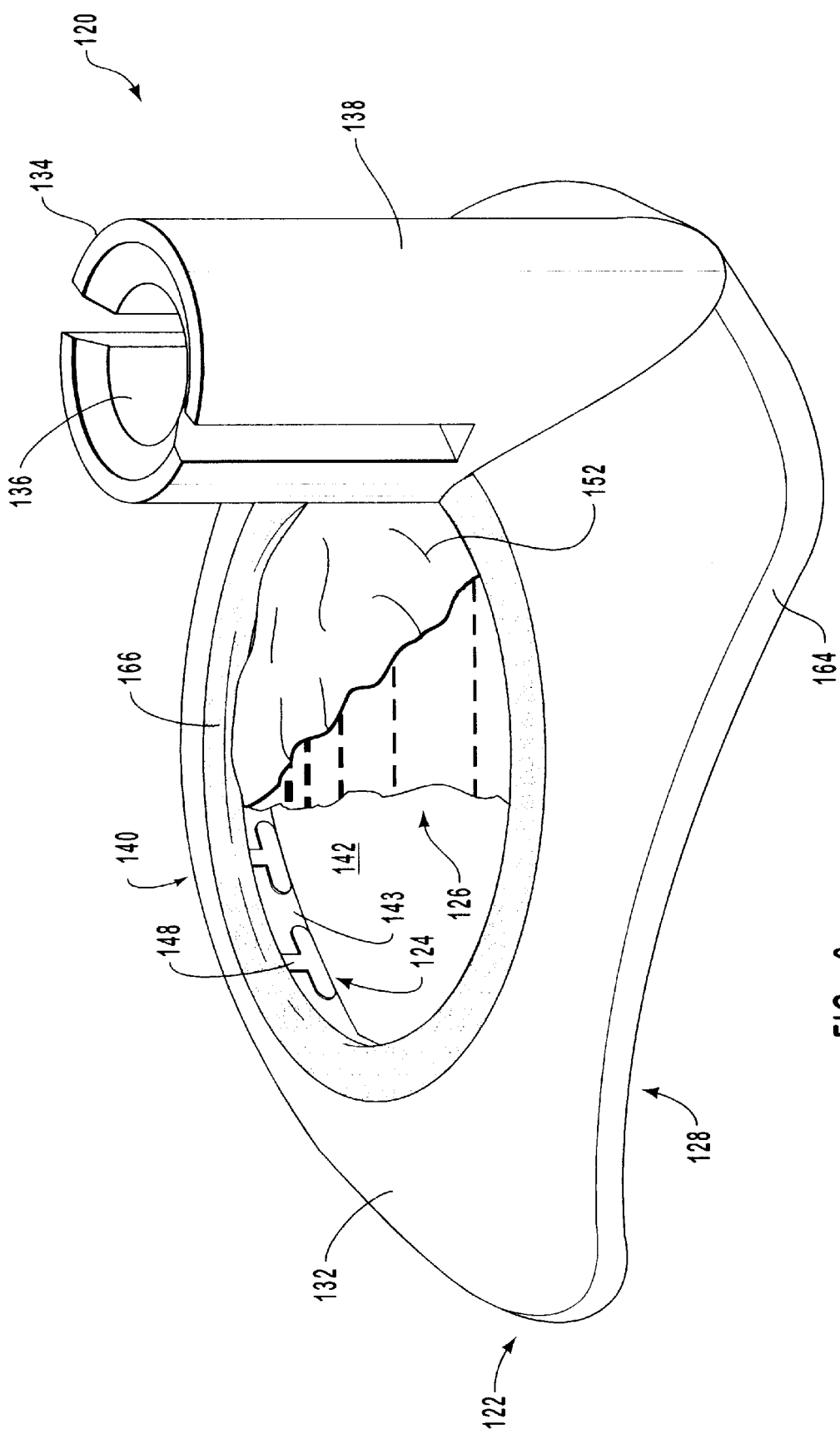
FIG. 6 is a perspective view of another embodiment of the iontophoretic apparatus of the present invention.

FIGS. 6–8 illustrate another embodiment of an ocular iontophoretic apparatus 120. The majority of the features previously discussed with respect to iontophoretic apparatus 20 also apply to the iontophoretic apparatus 120. Iontophoretic apparatus 120 has a housing element 122, a current distribution element 124, a medicament containment element 126, and a barrier element 128. Housing element 122 has a generally cup-shaped form, with a cup-shaped first portion 132, second end 134 and a middle portion 138. Cup-shaped first portion 132 is configured to comfortably be positioned about the eyeball, as shown in FIG. 8. Furthermore, the axis of cup-shaped first portion 132 is offset from the axis of second end 134, such that middle portion 138 extends from a peripheral edge of cup-shaped first portion 132. Cup-shaped first portion 132 has a hole 140 through the center thereof to allow access to the eyeball. In view of the teachings a contained herein, one skilled in the art can identify various other configurations capable of performing the intended function thereof.

For example, cup-shaped first portion 132 may be enclosed and completely covers the eyeball as seen in FIG. 7. In yet another configuration, middle portion 138 extends along the longitudinal axis of cup-shaped first portion 132. In other configurations, middle portion 138 may extend angularly from cup-shaped first portion 132. Other configurations of housing element 122 are equally effective in carrying out the intended function thereof. Housing element 122 is preferably formed from materials which will be easily manufactured while giving sufficient strength, rigidity, and connection flexibility for housing element 122. The types of material may range from plastics, composites, Teflon, nylon, polyester, polyethylene, and polycarbonates and the like. It is preferred that housing element 122 be composed of polycarbonates.

Current distribution element 124, as shown in FIG. 6, has a form similar to that of inner surface 143 of cup-shaped first portion 132. Current distribution element 124 has a segmented formed with a plurality of conductive extensions 148 that extend from a conductive ring (no shown). Current distribution element 124 therefore has a similar form to inner cavity 142 of cup-shaped first portion 132.

In general, the segmented form of current distribution element 124 provides spherical conformability benefits to ocular iontophoretic apparatus 120. The plurality of conductive extension 148 are capable of flexing in relation to the conductive ring and therefore conform to the surface of the eyeball while applying a pressure to the medicament containment element 126 to force the medicament containment element 126 against the surface of the eye. Various other configurations of current distribution element 124 are also effective in carrying out the intended function thereof.

For example, current distribution element 124 may be connected to a user handling device 130 (as shown in FIG. 5) such that one or more conductive extensions 148 pass through connector recess 136 and into inner cavity 142 of cup-shaped first portion 132. In another configuration, current distribution element 124 is positioned within connector recess 136 such that it comes into contact with medicament containment element 126. Current distribution element 124 may be positioned at any longitudinal position within connector recess 136, so long as it is configured to come into contact with medicament containment element 126. Various other configurations of current distribution element 124 are also capable of carrying out the intended function thereof. It will be appreciated by one skilled in the art that any type of current distribution element 124 may be used with appropriate modifications to housing element 122

According to another aspect of an alternate embodiment of the present invention, medicament containment element 126 has a cup-shaped member 152 which is formed to coincide with inner cavity 142 of cup-shaped first portion 132 while being provided with an interior curved portion that cooperates with the surface of the eye. Medicament containment element 126 has a double concaved shape with interior and exterior concaved curved profiles. The exterior concaved portion being shaped to cooperate with housing element 122, while the interior concaved portion cooperates with the surface of the eye. Medicament containment element 126 is coupled to current distribution element 124 and housing element 122, while being capable of conforming to the surface of the eye with which it is in contact. Various other configurations of medicament containment element are also effective in carrying out the intended function thereof.

For example, medicament containment element 126 may be formed with at least one aperture which is configured to cooperate with at least one conductive extension 148. In another configuration, medicament containment element 126 comprises a gel which is inserted within inner cavity 142 of cup-shaped first portion 132. In another configurations, medicament containment element 126 has a toroidal form such that hole 140 allows for continual refilling of medicament containment element 126. As such, medicant containment element 126 conforms to the surface upon which it is to contact. In view of the teachings contained herein, one skilled in the art can identify various other configurations of medicament containment element 126 which are capable of carrying out the intended function thereof.

According to another aspect of an alternate embodiment of the present invention, barrier element 128 comprises a cup-barrier portion 164. Cup-barrier portion 164 has a generally circular cross-section. Cup-barrier portion 164 is coupled to a lower external edge of cup-shaped first portion 132 such that it forms a seal with the eyeball when placed against the eyeball. Various other configurations of barrier element 128 are also effective in carrying out the intended function thereof.

For example, as shown in FIG. 6. in one alternate configuration, barrier element 128 comprises cup-barrier portion 164 and an upper cup-barrier portion 166. Upper cup-barrier portion 166 is coupled to the peripheral edge of hole 140 of cup-shaped first portion 132, while cup-barrier portion 164 is coupled to the lower peripheral edge of cup shaped first end 132. In combination, upper cup-barrier portion 166 and cup-barrier portion 164 create an inner recess which restricts medicament flow and thereby prevents medicament from passing into the inner portion of cup-shaped first portion 132 during certain medical procedures. Upper cup-barrier portions 166 and cup-barrier portion 164 may have the same cross-section or different cross-sections dependent on the medical procedure and needs of the apparatus. In view of the teaching contained herein, one skilled in the art can identify various other configurations of barrier element 128.

Figure 9:
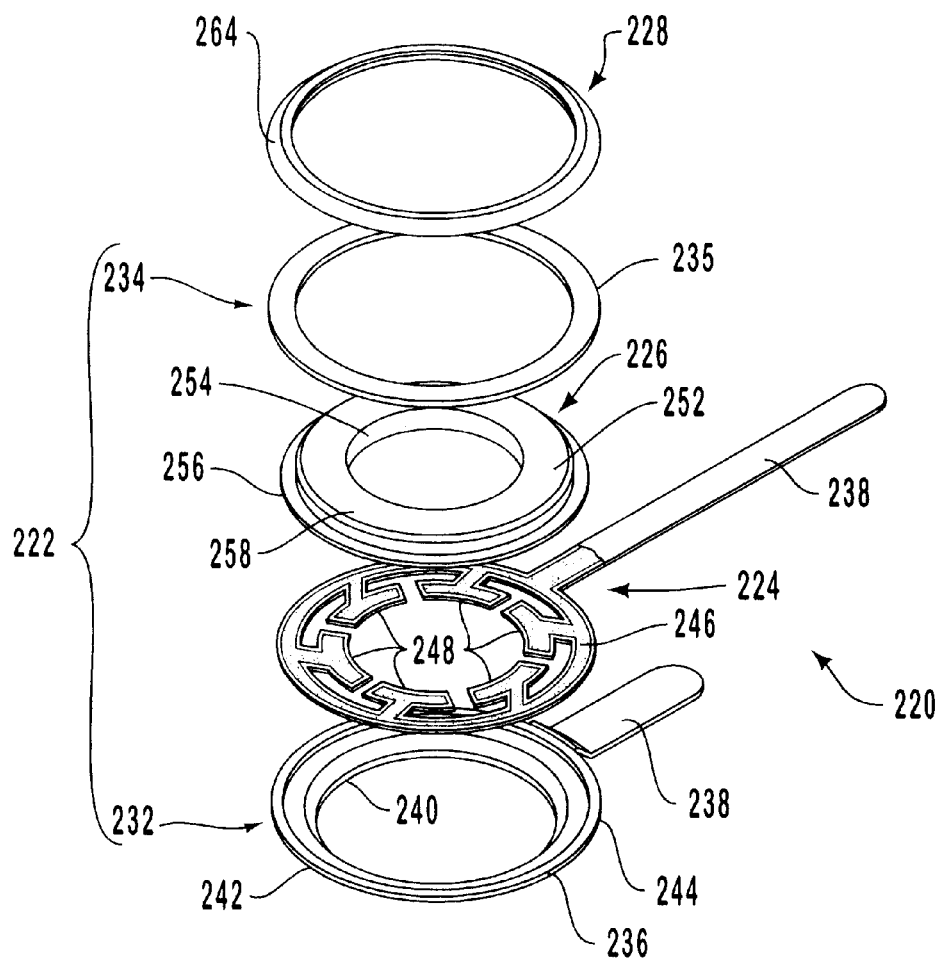
FIG. 9 is an exploded perspective view of another alternate embodiment of the iontophoretic apparatus of the present invention.
Figure 10:
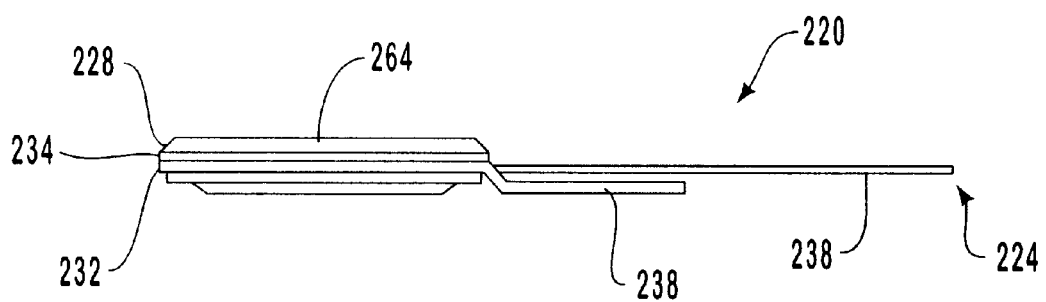
FIG. 10 is a side view of the embodiment of FIG. 9.
Figure 11:
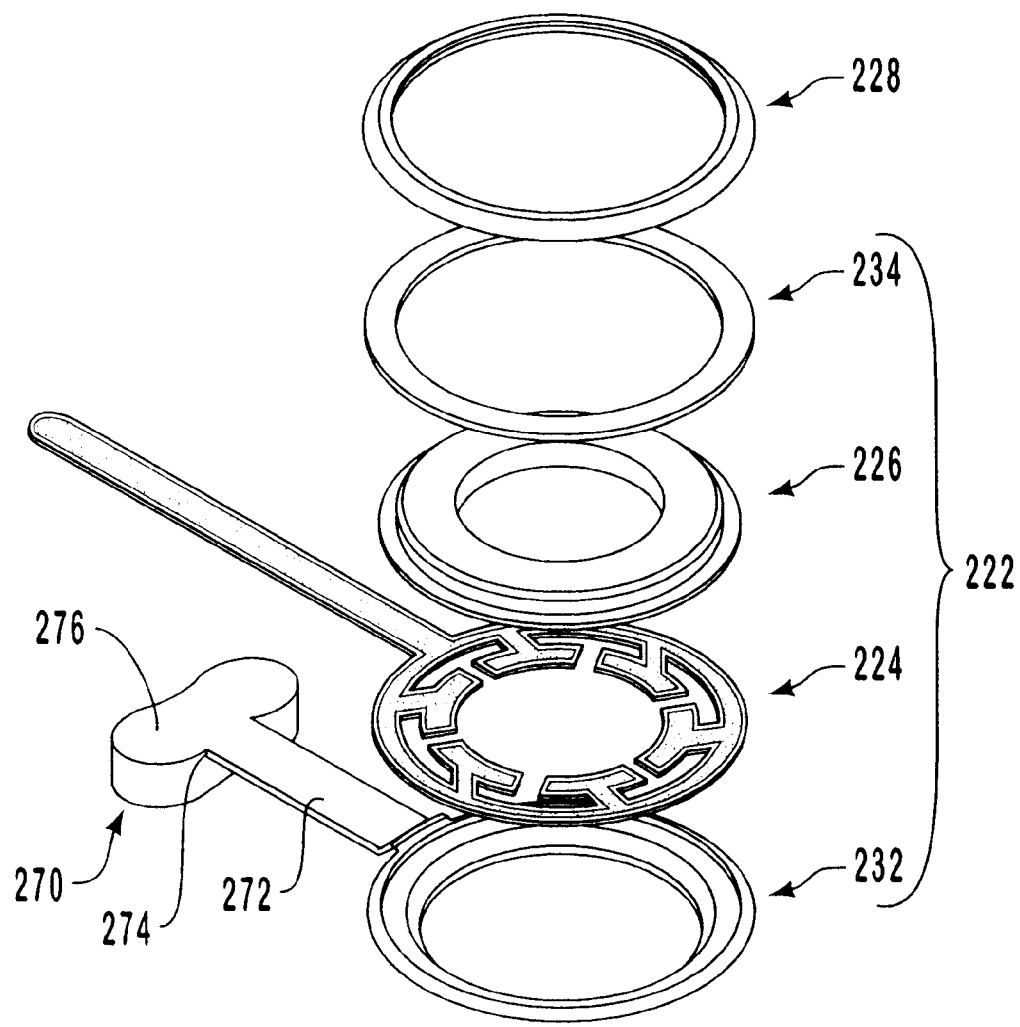
FIG. 11 is an exploded perspective view of another alternate embodiment of the invention.

FIGS. 9–11 illustrate another embodiment of an ocular iontophoretic apparatus 220. The majority of the features previously discussed with respect to iontophoretic apparatus 120 also apply to iontophoretic apparatus 220. Iontophoretic apparatus 220 has a housing element 222, a current distribution element 224, a medicament containment element 226, a barrier element 228, and a securing element 270. Each element has the same intended function as previously described.

Housing element 222 is formed from two separate pieces, a lower rim 232 and an upper rim 234. Lower rim 232 has a generally lower circular portion 236 with an arm 238 extending from the peripheral edge of lower circular portion 236. Lower rim 232 has an internal taper such that first lower end 240 has a smaller diameter than second lower end 242. Upper rim 234 has a generally circular upper portion 235 having a similar form to that of a washer. Upper rim 234 is used to securely hold medicament containment element 226 and current distribution element 224 to lower rim 232. It will be appreciated in view of the teachings contained herein, that one skilled in the art can identify various other configurations of housing element 222 which will perform the intended function thereof For example, lower rim 232 can have a flange 244 which extends from the peripheral edge of lower rim 232 parallel to the longitudinal axis thereof Flange 244 may then couple directly to upper rim 234 or a flange formed thereon to thereby securely hold current distribution element 224, medicament containment element 226, barrier element 228, and in an alternate configuration, securing element 270. Coupling may be performed through the use of sonic bonding, adhesives or other bonding techniques known to one skilled in the art. Various other configurations of upper rim 234 and lower rim 232 are also capable of carrying out the intended function thereof.

Upper rim 234 and lower rim 232 are preferably composed of materials which will be easily manufactured while giving sufficient strength and rigidity for housing element 222. The types of material may range from plastics, composites, Teflon, nylon, polyester, polyethylene, and polycarbonates and the like. It is preferred that upper rim 234 and lower rim 232 be substantially composed of polycarbonate.

Coupled with housing element 222 is current distribution element 224. Current distribution element 224 has a conductive ring portion 246 with a plurality of conductive extensions 248 extending from an inner peripheral edge thereof. The plurality of conductive extensions 248 extend toward the center of conductive ring portion 246 and are configured to flex when a force is applied thereto. Thus, current distribution clement 224 is capable of conforming to the surface of a patient's eye during iontophoresis. Current distribution element 224, furthermore, has an insulated portion 238 extending from the peripheral edge of ring portion 246. In one configuration, current distribution element 224 is formed from a printed film provide with metallic portions printed thereon. Various other configurations of current distribution element 224 are also capable of carrying out the intended function thereof.

For example, current distribution element 224 may include a single conductive extension 248. Current distribution element 224 may have other dimensions and shapes based on housing element 222, medicament containment element 226 and barrier element 228. If housing element 222 is rectangular, then current distribution element 224 may also be rectangular. Other configurations are also effective in carrying out the intended function thereof.

Current distribution element 224 is preferably manufactured from a thin metallic film, an acetate film with a metallic substance printed thereon. Other materials such as metals, conductive materials, printed plastics or films or the like are also effective in carrying out the intended function thereof. It is preferred that current distribution element 224 be composed of a polyester film. The thickness of the plastic sheets or films ranges from about 2 mils to about 4 mils. It is preferred that the thickness be from about 3 mils to about 4 mils. More preferably the thickness is approximately 3 mils.

In cooperation with current distribution element 224 is medicament containment element 226. Medicament containment element 226 has a body 252 having generally cylindrical form with a center hole 254 passing therethrough. The axis of center hole 254 coincides with longitudinal axis of body 254. A flange 256 extends from the lower peripheral edge of body 252 perpendicular to the longitudinal axis of body 252. Therefore, medicament containment element 226 has a generally L-shaped cross-section. Various other configurations of medicament containment element 226 are also effective in carrying out the intended function thereof.

In general, medicament containment element 226 is configured such that it may connect with current distribution element 224 and lower rim 232. Additionally, medicament containment element 226 allows upper rim 234 to securely fasten to lower rim 232 thereby sealing current distribution element 224 and medicament containment element 226 within housing element 222. Center hole 254 is provided, such that a portion of an eye may extend thereon while contacting a top surface 258.

In view of the teachings herein, one skilled in the art can identify various other configurations of medicant containment element 226. For example, in another configuration, medicament containment element 226 has no center hole 254, but is formed from a solid piece of material. In yet another configuration, medicament containment element 226 is formed from a gel. Furthermore, medicament containment clement 226 may have dimensions corresponding to those of housing element 222 and current distribution clement 224. For example, if housing element 222 has a curved form then medicament containment element 226 will either have a curved form or be formed from a material that allows conformability to a curved surface. Additionally, if current distribution element 224 has a single conductive extension 248, then medicament containment element 226 may have a corresponding aperture which cooperates with the conductive extension 248. It will be appreciated, in view of the teachings herein, that one skilled in the art can identify various other configurations of medicant containment element 226 that may perform the intended function thereof.

Medicament containment element 226, as previously discussed, may be manufactured from gel sponges, cross-linked hydrogels, gels or other similar materials. Other materials used to form medicament containment element 226 are known by one skilled in the art. It is preferred that medicament containment element 226 be composed of a compliant flexible gel or gel composite matrix which has a toroidal ring form or curved, spherical form as required for the particular treatment.

Coupled to housing element 222 and medicament containment element 226 is barrier element 228. Barrier element 228 has a generally circular body 264, with a generally bell-shaped cross section. Barrier element 228 interlocks with upper rim 234 and/or medicament containment element 226 to thereby retain medicament containment element 226. Barrier element 228, in one configuration, extends beyond the horizontal plane of the top surface 258 of medicament containment element 226 by extending beyond the horizontal plane of top surface 258. Barrier element 228 contacts the surface of the eye prior to medicament containment element 226 and provides the sealing function previously described Various other configurations of barrier element 228 are known by one skilled in the art in view of the teaching contained herein.

For example, barrier element 228 may be configured such that when lower rim 232 securely holds medicament containment element 226 and/or current distribution element 224, barrier element 228 coincides with or is positioned below the horizontal plane of top surface 258 of medicament containment element 226. In other configurations, barrier element 228 may have various cross-sections, known by one skilled in the art, to form a seal when barrier element 228 comes into contact with the eye. Additionally, the location of barrier element 228 is dependent on the particular use to which the iontophoretic apparatus 220 is to be used as has previously been discussed. Furthermore, iontophoretic apparatus 220 may be formed with a second barrier element that is coupled to the inner surface of center hole 254 to isolate an area of the eye such as, by way of example and not limitation, the cornea from the introduction of medicament. It can be appreciated that use of a second barrier may aid in the introduction of medicament to a specific location which is to be phoresed.

According to another aspect of an alternate embodiment of the present invention, iontophoretic apparatus 220 comprises securing element 270. Securing element 270, in one illustrative configuration as shown in FIG. 11, has a securing arm 272 extending from the peripheral edge of lower rim 232 and an attachment portion 276 coupled to a distal end 274 of securing arm 272. Attachment portion 276 has a bonding material coupled thereto to fixably attach to an individual's cheek, forehead or other part of a person's body. Various other configurations of securing element 270 are also effective in carrying out the intended function thereof.

For example, securing element 270 may not be coupled to upper rim 234, In an alternative configuration, securing element 270 has a generally circular body coupled to securing arm 272. The body has a hole therethrough which may connect to the outer surface of lower rim 232 and surround lower rim 232. In another configuration, securing body may be located between upper rim 234 and lower rim 232 and be fixably connected to housing element 222 when upper rim 234 is coupled to lower rim 232. In yet another configuration, securing arm 272 may be formed from a harness which may be coupled to a patient's head, shoulders or other part of the patient's body to hold iontophoretic apparatus 220 during iontophoresis. Still yet another configuration, securing arm 272 is configured to allow a user to manually hold iontophoretic apparatus 20 in place. In yet another configuration attachment portion 276 may be affixed through the use of adhesives or other similar technique such that securing element 270 may be easily removed without causing damage to the patient's body. In view of the teachings contained herein, one skilled in the art can identify various )ther configurations of securing element 270.

Securing element 270 is preferably composed of materials which will be easily manufactured while giving sufficient strength and rigidity. The types of material may range from plastics, metals, composites, Teflon, nylon, polyester, polyethylene, and polycarbonates and the like. It is preferred that securing element 270 be substantially composed of polycarbonate.

Figure 12:
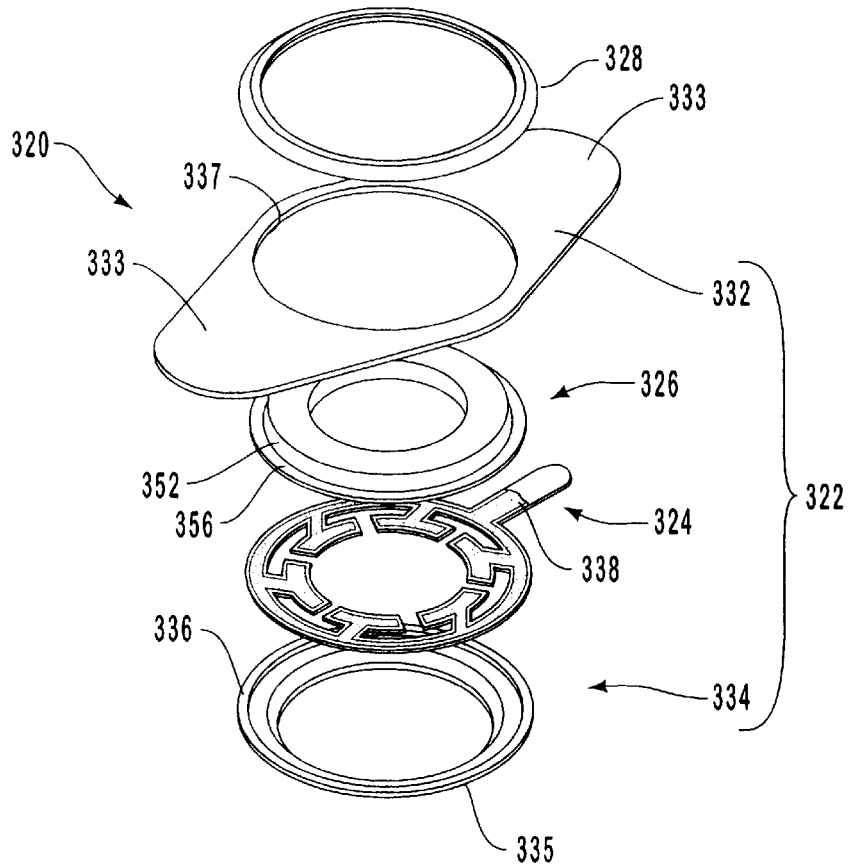
FIG. 12 is an exploded perspective view of yet another embodiment of the iontophoretic apparatus of the present invention.
Figure 13:
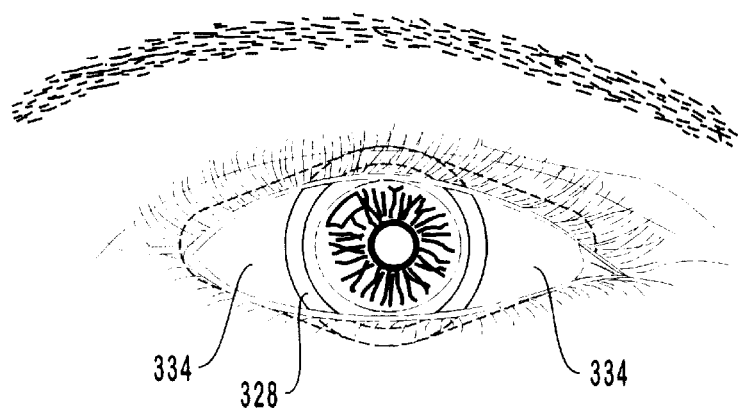
FIG. 13 is a plan view of the embodiment of FIG. 12.

FIGS. 12–13 illustrate another embodiment of an ocular iontophoretic apparatus 320. The majority of the features previously discussed with respect to iontophoretic apparatus 220 also apply to iontophoretic apparatus 320. Iontophoretic apparatus 320 has a housing element 322, a current distribution element 324, a medicament containment element 326 and a barrier element 328. Housing element 322 comprises a body portion 332 and an upper rim 334. Body portion 332 is configured with at least one wing portion 333. Body portion 332 and wing portions 333 are configured to be flexible to allow wing portions 333 to extend underneath the eyelids of the patient when in use as shown in FIG. 12. Body portion 332 is further configured with an orifice 337 which is formed to cooperate with medicant containment element 326 to allow the cornea of the eye to extend therethrough.

Upper rim 334 has a generally circular form with a rim flange 336 extending from a rim body 335. Flange 336 couples to the lower surface of body portion 332 and aids in the retention of medicament containment element 326 and current distribution element 324 again body portion 332. Various alternative configurations of housing element 332 are also effective in carrying out the intended function thereof.

Housing element 322 is preferably composed of materials which will be easily manufactured while giving sufficient strength and flexibility to be located beneath the eyelids of a patient. The types of material may range from plastics, metals, composites, Teflon, nylon, polyester, polyethylene, and polycarbonates and the like.

Other elements of this embodiment are similar to those previously discussed while being coupled together in a similar manner. For example, current distribution element 324 is formed with a reduced insulated portion 338. Reduced insulated portion 338 is much shorter than the insulated portion 238 of iontophoretic apparatus 220 to prevent injury to the eye because of penetration from the end thereof. Medicament containment element 326 has basically the same configuration as medicament containment element 326; however, in use, body 352 of medicament containment element 326 protrudes through orifice 337 and flange 356 rests upon a lower surface 338 of body portion 332. Therefore, medicament containment element 326 has a generally inverted L-shaped cross-section. Flange 356 is further configured to cooperate with current distribution element 324 which is coupled thereto. Barrier clement 328 couples to the portion of medicament containment element 326 which extends through orifice 337. Various other configurations of medicament containment element 326 are known to one skilled in the art to carry out the intended function thereof.

Figure 17:
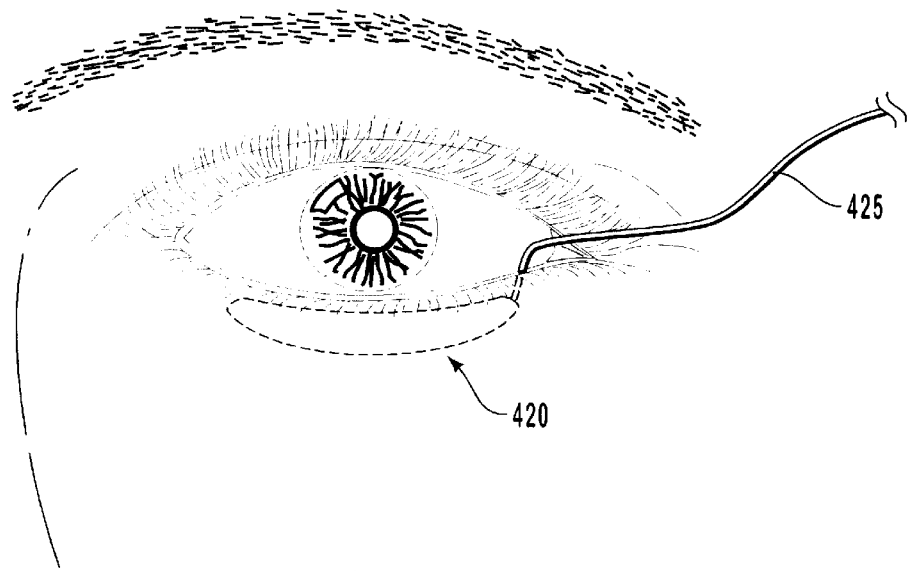
FIG. 17 is a plan view of the embodiment of FIG. 14 in use.

FIGS. 14–18 illustrate another embodiment of an ocular iontophoretic apparatus 420. The majority of the features previously discussed with respect to other iontophoretic apparatus also apply to iontophoretic apparatus 420. Iontophoretic apparatus 420 in general is formed to be easily located either at the temporal side of the eye socket, as shown in FIG. 16, or underneath the lower eyelid, as shown in FIG. 17, and be held in place by the frictional forces exerted by the surrounding tissues while providing the necessary iontophoretic delivery of a medicament. In the configuration depicted herein no adhesives are necessary to retain iontophoretic apparatus 420 in place because the eyelid or surrounding tissues maintain frictional contact with the iontophoretic apparatus 420, thereby preventing movement of iontophoretic apparatus 420.

Referring now to FIGS. 14 and 15, a configuration of iontophoretic apparatus 420 which is to be used at the temporal side of the eye socket is depicted. Iontophoretic apparatus 420 includes a housing element 422 that is in cooperation with a current distribution element 424 that is linked via a wire 425 to a power supply (not shown). Coupled thereto is a medicament containment element 426 and a barrier element 428. Housing element 422 comprises a generally triangular formed body portion 432 with a securing element 434 coupled at one side thereof. Body portion 432 is configured to retain current distribution element 424, medicament containment element 426 and barrier element 428 for easily manipulation and insertion while being characterized as being impervious to the migration of medicament or electrical current. Therefore, body portion 432 prevents medicament from being passed therethrough to enter the surrounding tissues.

Figure 18:
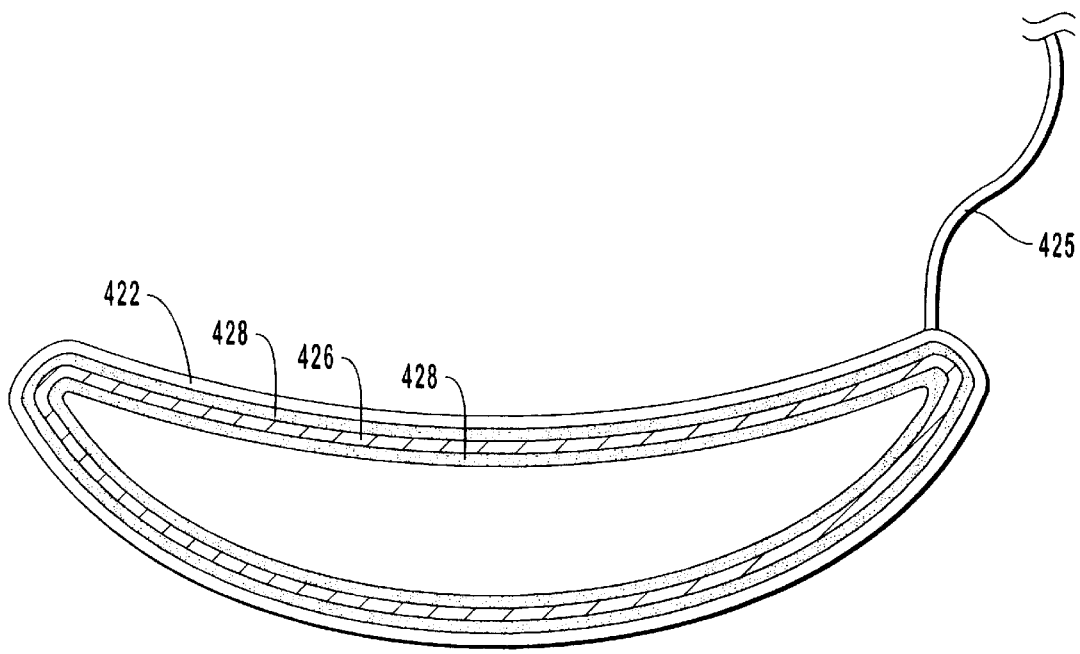
FIG. 18 is a plan view of an alternate configuration of the embodiment of FIG. 14.

In the configuration of FIG. 14, housing element 422 is provided with a securing element 434 to aid the frictional forces in releasably positioning iontophoretic apparatus 420. Securing element 434 has a generally hooked form such that upon insertion of iontophoretic apparatus 420 at the temporal side of the eye socket securing element 434 cooperates with the corner or the eye as shown in FIG. 16. In other configurations of the present invention, the end of securing element 434 may be formed with an adhesive patch which may be used to releasably couple iontophoretic apparatus 420 in place. In still other configurations, housing element 422 is formed without securing element 434, as shown in FIG. 18. In view of the teaching contained herein, one skilled in the art can identify various other configurations of housing element 422 which are also capable of performing the desire function thereof.

For example, the size and dimensions of iontophoretic apparatus 420 may be varied as necessary to perform the necessary iontophoresis. As shown in FIGS. 17 and 18, housing element 422 can have an elongated form to cooperate and accommodate insertion under the lower eyelid. Housing element 422 and therefore Iontophoretic apparatus 420 may have various cross-sectional forms such as, but not limited to, circular, ovular, rectangular, square, trapezoidal, or the like.

In general, housing element 422 may be created from various types of material so long as they are flexible and prevent migration of electrical current and medicament therethrough during iontophoresis. The materials may include, but are not limited to, flexible plastics, films, composites, Teflon, nylon, polyester, polyethylene, polycarbonates, rubbers. elastomers, silicones, and the like. It is preferred that housing element 422 be substantially formed from a flexible silicone.

Current distribution element 424, in this embodiment is integrally formed with housing element 422. As shown in FIGS. 14 and 15 by way of a dotted line, current distribution element 424 takes the form of an electrically conductive printed ink that is formed on the inner surface of housing element 422. Through this configuration the flexibility of iontophoretic apparatus 420 is increased since the number of layers utilized to form the iontophoretic apparatus is decreased. Other configurations of current distribution element 424 are known by one skilled in the art, in view of the teaching contained herein.

In use, as shown in FIG. 16, iontophoretic apparatus 420 is slipped between the orbit sides (not shown) and the eyeball. Housing element 422 contacts the surface of the orbit while medicament containment element 426 and barrier element 428 contacts the eyeball. During positioning of iontophoretic apparatus 420, securing element 434 cooperates with the corner of the eye such that the end of securing element 434 attaches to the surrounding tissue of the eye. By so doing securing element 434 prevents movement of iontophoretic apparatus 420 during operation.

As shown in FIGS. 17 and 18, another configuration of iontophoretic apparatus 420 is shown wherein securing element 434 is eliminated from housing element 422. In this way iontophoretic apparatus 420 is retained in place by the frictional forces applied by the lower eyelid upon the surface of housing element 422.

In view of the teaching contained herein, one skilled in the art can identify various other configurations. For example, as shown in FIG. 18, iontophoretic apparatus 420 is formed with two barrier elements 428 to form a sealed interior space wherein medicament containment element 426 is located.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In iontophoretic apparatus comprising:
    a housing element;
    a current distribution element coupled to said housing element;
    a medicament containment element coupled to said current distribution element; and
    a barrier element surrounding said medicament containment element and configured to be placed in contact with a patient's eye tissue, and to reduce current flow outside of said barrier element, wherein the current distribution element, the medicament element and barrier element are sufficiently thin and flexible so as to facilitate operable positioning and retention of a least a portion of the current distribution element and the medicament containment element between the eyelid and eyeball of a patient.

2. An iontophoretic apparatus as recited in claim 1, wherein said iontophoretic apparatus further comprises a securing element configured to hold said iontophoretic apparatus in contact with a patient's tissue.

3. An iontophoretic apparatus as recited in claim 1, wherein said housing element is flexible.

4. An iontophoretic apparatus as recited in claim 1, wherein said current distribution element is formed from:
    (a) a conductive portion; and
    (b) a plurality of conductive extensions, said plurality of conductive extensions being flexibly attached to said conductive portion.

5. An iontophoretic apparatus as recited in claim 1, wherein said current distribution element is formed on a surface of said housing element.

6. An iontophoretic apparatus as recited in claim 1, wherein said current distribution element and said medicament containment element conform to a surface upon which said medicament containment element is in contact during iontophoresis.

7. An iontophoretic apparatus as recited in claim 1, wherein said housing element conforms to the surface upon which said medicament containment element is in contact during iontophoresis.

8. An iontophoretic apparatus as recited in claim 1, wherein said medicament containment element is configured to hold a medicament while releasing said medicament under influence of an electrical potential.

9. An iontophoretic apparatus as recited in claim 1, wherein said barrier element is further configured to prevent infiltration of contaminants from outside of said barrier to the interior thereof.

10. An iontophoretic apparatus as recited in claim 1, wherein said barrier element is further configured to prevent medicament from flowing outside of said barrier element.

11. In iontophoretic apparatus comprising:
    a housing element;
    a flexible current distribution element supported by said housing element;
    a confirmable medicament containment element coupled to said current distribution element and said housing element; and
    a barrier element surrounding said medicament containment element and configured to reduce current flow outside of said barrier element, wherein the current distribution element, the medicament element and barrier element are sufficiently thin and flexible so as to facilitate operable positioning and retention of a least a portion of the current distribution element and the medicament containment element between the eyelid and eyeball of a patient.

12. An iontophoretic apparatus as recited in claim 11, wherein said iontophoretic apparatus further comprises a securing element configured to hold said barrier element and said medicament containment element in contact with a patient's tissue.

13. An iontophoretic apparatus as recited in claim 11, wherein said barrier element cooperates with said current distribution element, said medicament containment element, and said housing element to reduce current flow outside of said barrier element and aid in the preferential delivery of medicament.

14. An iontophoretic apparatus as recited in claim 13, wherein said barrier element is further provided to prevent infiltration of contaminants into the interior of said barrier element.

15. An iontophoretic apparatus as recited in claim 11, wherein said housing element is flexible and formed to conform to a patient's tissue.

16. An iontophoretic apparatus as recited in claim 15, wherein said current distribution element is formed on a first surface of said housing element.

17. An iontophoretic apparatus as recited in claim 16, wherein said current distribution element and said medicament containment element conform to the patient's tissue upon which said medicament containment element is in contact during iontophoresis.

18. An iontophoretic apparatus as recited in claim 17, wherein said iontophoretic apparatus is retained in place by frictional forces applied to a second surface of said housing element by tissues surrounding said housing element.

19. A method of positioning an iontophoretic apparatus comprising the steps of:
    providing an iontophoretic apparatus having
        a housing element;
        a current distribution element coupled to said housing element;
        a medicament containment element coupled to said current distribution element; and
        a barrier element associated with the medicament containment element;
    positioning at least a portion of the medicament containment element and the barrier element on a patient's eye tissue; and
    positioning at least a portion of the eyelid surrounding a patient's eye over at least a portion of the medicament containment element and the barrier element.

* * * * *